(12) United States Patent
Mijers

(10) Patent No.: US 7,717,116 B2
(45) Date of Patent: May 18, 2010

(54) APPARATUS FOR CONNECTING A RESPIRATORY DEVICE WITH A PATIENT

(75) Inventor: Jan W. Mijers, Heemstede (NL)

(73) Assignee: Filtertek Inc., Hebron, IL (US)

( * ) Notice: Subject to any disclaimer, the term of this patent is extended or adjusted under 35 U.S.C. 154(b) by 785 days.

(21) Appl. No.: 11/633,271

(22) Filed: Dec. 4, 2006

(65) Prior Publication Data

US 2007/0163599 A1 Jul. 19, 2007

Related U.S. Application Data

(63) Continuation of application No. PCT/EP2005/006114, filed on Jun. 7, 2005.

(51) Int. Cl.
*A61M 16/00* (2006.01)

(52) U.S. Cl. .............. 128/207.15; 128/207.14; 128/204.18; 128/205.24; 137/102; 137/112; 604/48; 604/99.02

(58) Field of Classification Search ............ 128/204.18, 128/205.24, 206.29, 207.12–207.29; 137/102, 137/112, 908; 604/509, 98.01–102.03
See application file for complete search history.

(56) References Cited

U.S. PATENT DOCUMENTS

| | | |
|---|---|---|
| 2,630,874 A | 3/1953 | Langdon |
| 2,758,609 A | 8/1956 | Dickert et al. |
| 2,980,032 A | 4/1961 | Schneider |
| 3,084,707 A | 4/1963 | Frye |
| 3,238,056 A | 3/1966 | Pall et al. |
| 3,270,771 A | 9/1966 | Morgan et al. |
| 3,599,657 A | 8/1971 | Maldays |
| 3,623,504 A | 11/1971 | Davis |
| 3,633,605 A | 1/1972 | Smith |
| 3,658,183 A | 4/1972 | Best et al. |
| 3,779,274 A | 12/1973 | Kelly |
| 3,782,083 A | 1/1974 | Rosenberg |

(Continued)

FOREIGN PATENT DOCUMENTS

BE 1 009 834 A6 10/1997

(Continued)

OTHER PUBLICATIONS

Christians, Rolf, "Membranen in der Pneumatik," *Fluid*, pp. 39-46 (Apr. 1980).

(Continued)

*Primary Examiner*—Danton DeMille
*Assistant Examiner*—Rachel T Young
(74) *Attorney, Agent, or Firm*—Brinks Hofer Gilson & Lione

(57) ABSTRACT

An apparatus for connecting a respiratory device with a patient is provided, including a breathing tube for insertion into a patient's trachea, an inflatable cuff positioned around the breathing tube, a connection tube connected to the cuff for providing inflating air flow thereto, a pressurized air reservoir, and a valve connected to the pressurized air reservoir and to the proximal end of the connection line. The valve includes an entry port associated with an entry differential force chamber, a first exit port associated with a first differential force chamber and coupled with the connection line, a second exit port associated with a second differential force chamber and coupled with the pressurized air reservoir, and a flexible membrane selectively sealingly separating the differential force chambers. The flexible membrane is configured to selectively connect the first and second differential force chambers to maintain a substantially constant air pressure in the cuff.

20 Claims, 3 Drawing Sheets

U.S. PATENT DOCUMENTS

| | | |
|---|---|---|
| 3,794,043 A | 2/1974 | McGinnis |
| 3,932,153 A | 1/1976 | Byrns |
| 3,966,520 A | 6/1976 | Fallenbeck et al. |
| 4,022,258 A | 5/1977 | Steidley |
| 4,089,349 A | 5/1978 | Schenk |
| 4,141,379 A | 2/1979 | Manske |
| 4,148,732 A | 4/1979 | Burrow et al. |
| 4,159,722 A * | 7/1979 | Walker ................ 137/496 |
| 4,178,940 A * | 12/1979 | Au ................ 128/207.15 |
| 4,181,477 A | 1/1980 | Litt |
| 4,188,978 A | 2/1980 | De Lorenzo |
| 4,237,880 A | 12/1980 | Genese |
| 4,241,756 A | 12/1980 | Bennett et al. |
| 4,343,305 A | 8/1982 | Bron |
| 4,355,639 A | 10/1982 | Di Salvo |
| 4,404,006 A | 9/1983 | Williams et al. |
| 4,415,003 A | 11/1983 | Paradis et al. |
| 4,459,139 A | 7/1984 | von Reis et al. |
| 4,534,764 A | 8/1985 | Mittleman et al. |
| 4,556,086 A | 12/1985 | Raines |
| 4,593,720 A | 6/1986 | Bergandy |
| 4,630,606 A | 12/1986 | Weerda et al. |
| 4,646,781 A | 3/1987 | McIntyre |
| 4,664,800 A | 5/1987 | Raines et al. |
| 4,670,510 A | 6/1987 | Kobayashi et al. |
| 4,712,583 A | 12/1987 | Pelmulder et al. |
| 4,749,003 A | 6/1988 | Leason |
| 4,754,899 A | 7/1988 | Stull |
| 4,768,547 A | 9/1988 | Danby et al. |
| 4,793,503 A | 12/1988 | Towns et al. |
| 4,825,862 A | 5/1989 | Sato et al. |
| 4,846,215 A | 7/1989 | Barree |
| 4,874,513 A | 10/1989 | Chakraborty et al. |
| 4,958,661 A | 9/1990 | Holtermann et al. |
| 4,966,199 A | 10/1990 | Ruschke |
| 4,986,904 A | 1/1991 | Bugar et al. |
| 5,011,555 A | 4/1991 | Sager |
| 5,025,829 A | 6/1991 | Edwards et al. |
| 5,041,105 A | 8/1991 | D'Alo et al. |
| 5,125,522 A | 6/1992 | Pezzoli et al. |
| 5,147,545 A | 9/1992 | Despard et al. |
| 5,215,538 A | 6/1993 | Larkin |
| 5,230,727 A | 7/1993 | Pound et al. |
| 5,265,770 A | 11/1993 | Matkovich et al. |
| 5,269,917 A | 12/1993 | Stankowski |
| 5,443,723 A | 8/1995 | Stankowski et al. |
| 5,453,097 A | 9/1995 | Paradis |
| 5,500,003 A | 3/1996 | Guala et al. |
| 5,505,326 A | 4/1996 | Junko |
| 5,520,661 A | 5/1996 | Lal et al. |
| 5,556,541 A | 9/1996 | Ruschke |
| 5,603,792 A | 2/1997 | Guala et al. |
| 5,617,897 A | 4/1997 | Myers |
| 5,695,638 A | 12/1997 | Gutiz et al. |
| 5,749,861 A | 5/1998 | Guala et al. |
| 5,771,935 A | 6/1998 | Myers |
| 5,782,383 A | 7/1998 | Robinson |
| 5,935,100 A | 8/1999 | Myers |
| 6,086,762 A | 7/2000 | Guala |
| 6,168,653 B1 | 1/2001 | Myers |
| 6,290,682 B1 | 9/2001 | Myers |
| 6,464,870 B1 | 10/2002 | Castellanos et al. |
| 6,579,342 B2 | 6/2003 | Wang |
| 6,708,714 B1 | 3/2004 | Mijers |
| 6,779,669 B2 | 8/2004 | Schann |
| 2002/0144595 A1 | 10/2002 | Wang et al. |
| 2004/0074925 A1 | 4/2004 | Faurie |
| 2004/0153047 A1 | 8/2004 | Blank et al. |

FOREIGN PATENT DOCUMENTS

| | | |
|---|---|---|
| DE | 48105 | 6/1888 |
| DE | 667 675 | 4/1934 |
| DE | 1 695 553 | 5/1971 |
| DE | 1 675 370 | 9/1971 |
| DE | 25 02 673 A1 | 7/1976 |
| DE | 25 13 350 A1 | 10/1976 |
| DE | 27 13 618 C2 | 10/1977 |
| DE | 29 19 343 A1 | 11/1980 |
| DE | 30 35 301 A1 | 4/1981 |
| DE | 29 49 262 A1 | 6/1981 |
| DE | G 82 14 927.5 U1 | 9/1982 |
| DE | 32 15 329 A1 | 12/1982 |
| DE | 33 27 342 A1 | 2/1985 |
| DE | 34 35 900 A1 | 4/1986 |
| DE | G 86 03 917.2 U1 | 5/1986 |
| DE | 36 32 412 A1 | 3/1988 |
| DE | 38 03 380 A1 | 8/1989 |
| DE | 40 39 814 A1 | 6/1992 |
| DE | 92 09 491.0 U1 | 10/1992 |
| DE | 41 42 494 A1 | 7/1993 |
| DE | 42 01 258 A1 | 7/1993 |
| DE | G 93 19 810.8 U1 | 3/1994 |
| DE | 43 09 262 A1 | 6/1994 |
| DE | 43 04 949 A1 | 8/1994 |
| DE | G 93 10 673.4 U1 | 9/1994 |
| DE | 43 15 701 A1 | 11/1994 |
| DE | G 295 01 239.0 U1 | 4/1995 |
| DE | 691 09 240 T2 | 10/1995 |
| DE | G 196 05 217.3 | 2/1996 |
| DE | G 296 10 419.1 | 12/1996 |
| DE | 195 45 421 A1 | 6/1997 |
| DE | 196 43 360 C1 | 5/1998 |
| DE | 197 49 562 C1 | 4/1999 |
| DE | 195 45 421 C2 | 5/2001 |
| DE | 102 19 994 A10 | 12/2003 |
| DE | 20 2004 009 831 U1 | 9/2004 |
| DE | 20 2004 009 521 U1 | 10/2004 |
| DE | 10 2004 053 214 A1 | 1/2006 |
| EP | 0 072 800 B1 | 3/1983 |
| EP | 0 379 047 A1 | 7/1990 |
| EP | 0 459 498 A1 | 12/1991 |
| EP | 0 562 246 A1 | 9/1993 |
| EP | 0 612 537 A2 | 8/1994 |
| EP | 0 612 537 A3 | 8/1994 |
| EP | 0 652 018 B1 | 5/1995 |
| EP | 0 812 596 A1 | 12/1997 |
| EP | 0 878 628 A2 | 11/1998 |
| EP | 0 887 085 A2 | 12/1998 |
| EP | 0 934 757 A2 | 8/1999 |
| EP | 1 063 956 B1 | 1/2001 |
| EP | 1 088 765 A1 | 4/2001 |
| EP | 1 093 828 A2 | 4/2001 |
| EP | 1 099 457 A2 | 5/2001 |
| EP | 1 239 145 B1 | 5/2007 |
| FR | 2 666 745 A1 | 3/1992 |
| GB | 439 278 A1 | 12/1935 |
| GB | 811 818 | 4/1959 |
| GB | 2 027 168 A1 | 2/1980 |
| NL | 293686 | 4/1965 |
| WO | WO 88/02639 | 4/1988 |
| WO | WO 89/02764 | 4/1989 |
| WO | WO 91/11641 | 8/1991 |
| WO | WO 93/10015 A1 | 5/1993 |
| WO | WO 96/03166 A1 | 2/1996 |
| WO | WO 97/03712 | 2/1997 |
| WO | WO 97/47339 | 12/1997 |

OTHER PUBLICATIONS

PCT English language translation of International Preliminary Report on Patentability for PCT/EP2005/006114; Jun. 7, 2005; 7p; The International Bureau of WIPO; Geneva, Switzerland.

"Design for assembly"; http://web.archive.org/web/20021026013912/ http://www.scudc.scu.edu/cmdoc/dg_doc/develop/design/part/33000004.htm; Allegedly archived Oct. 26, 2002; 10 pages.

"Handbook of Plastics Joining: A Practical Guide"; William Andrew, Inc.; 1997; pp. 121-124; Plastics Design Library; New York, USA.

* cited by examiner

US 7,717,116 B2

APPARATUS FOR CONNECTING A RESPIRATORY DEVICE WITH A PATIENT

CROSS-REFERENCE TO RELATED APPLICATION

This patent application is a continuation of International Application PCT/EP2005/006114 published as PCT patent application WO 2005/120618 A1, with an international filing date of Jun. 7, 2005 and entitled "DEVICE FOR CONNECTING A RESPIRATOR TO A PATIENT," which claims the benefit of priority to German patent application DE 102004027734 A1, filed Jun. 7, 2004 and entitled "Vorrichtung zur Verbindung eines Beatmungsgerätes mit dem Patienten," the entire contents of each of which are incorporated herein by reference.

FIELD OF THE INVENTION

This invention relates to an apparatus for connecting a respiratory device with a patient.

BACKGROUND

This invention relates to an apparatus for connecting a respiratory device with a patient having a breathing tube, such as an endotracheal tube or tracheostomy tube. The breathing tube is insertable into the patient's trachea and is connected to a source of breathing gas, such as air or oxygen. An inflatable cuff surrounds a portion of the breathing tube adjacent to the distal end of the breathing tube. When inflated, the cuff forms a seal with the inner walls of the patient's trachea, thereby preventing the breathing gas from escaping through the patient's mouth. Specifically, the inflatable cuff is connected to a connection line which provides an inflation gas, such as air or oxygen. When inflated, the cuff forms a generally air-tight seal with the patient's trachea so the breathing gas delivered from the breathing tube is forced to flow towards the patient's lungs rather than back up his/her trachea. It is desirable to control the air pressure within the cuff in order to maintain a seal between the cuff and the patient's trachea and in order to minimize or reduce the risk of over-inflating the cuff and causing trauma to the patient's trachea.

One currently-known apparatus for regulating the pressure in the cuff is disclosed in U.S. Pat. No. 3,794,043 (the '043 patent). The '043 patent discloses an apparatus used for the artificial respiration of patients. After the breathing tube has been inserted into the trachea of the patient, a syringe is connected to a valve for inflating the cuff to a pressure between 16 and 25 millimeters of Mercury. Simultaneously with the inflation of the cuff, a pressurized air reservoir connected to the valve is also filled. After removal of the syringe, the valve maintains a constant pressure in the cuff by pressure differentiation between the cuff and the air reservoir. This arrangement is such that the air from the pressurized air reservoir can flow back to the cuff comparatively easily while the air in the opposite direction, i.e. from the cuff to the pressurized air reservoir, should be with a reduced flow rate to prevent leaks from occurring between the cuff and the trachea.

Although this design performs in a satisfactory manner, it is relatively complex and expensive to produce, and it requires relatively sensitive materials. For example, the valve in this design includes two housings positioned within each other, where the inner housing receives a mushroom-shaped body serving as a valve member, with bottom end thereof forming the sealing surface of the check valve that controls entry of air into the valve. A separate push rod, which is made of plastic, is provided for actuating the check valve. During the filling of the cuff, by means of the syringe, the check valve has to be displaced to open the valve. This design includes a relatively high number of parts and is relatively complex, both of which may be disadvantageous.

Additionally, the mushroom-shaped body serving as the valve member is made of a natural rubber. Specifically, the rubber balloon is clamped and fixed at the valve body between the two housings positioned within each other and the head of the mushroom shaped valve body is positioned within the balloon of natural rubber in combination with its margin engaging the top side of the valve and relief openings within the head the part is acting as a control valve. It is undesirable to use natural rubber because it may be subject to premature wear.

It is therefore desirable to provide an apparatus for connecting a respiratory device with a patient having reduced part complexity and reduced manufacturing costs, as well as improved durability and potentially reduced part wear.

BRIEF SUMMARY

This invention seeks to address the above-mentioned shortcomings of the prior art. An apparatus for connecting a respiratory device with a patient is provided, including a breathing tube for insertion into a patient's trachea, an inflatable cuff surrounding around a distal portion of the breathing tube, a connection connected to the cuff for providing inflating air flow thereto, a pressurized air reservoir having an adjustable volume, and a valve connected to the pressurized air reservoir and to the proximal end of the connection line. The valve includes an entry port associated with an entry differential force chamber and configured to be coupled with a syringe, a first exit port associated with a first differential force chamber and configured to be coupled with the proximal end of the connection line, a second exit port associated with a second differential force chamber and configured to be coupled with the pressurized air reservoir, and a flexible membrane selectively sealingly separating the first differential force chamber, the second differential force chamber, and the entry differential force chamber from each other. The flexible membrane is configured to selectively connect the first differential force chamber and the second differential force chamber so as to maintain a substantially constant air pressure in the cuff.

In one aspect, the flexible membrane is a three-way check valve. The flexible membrane operates as a first check valve to regulate airflow between the entry differential force chamber and the first differential force chamber. The flexible membrane also operates as a second check valve to regulate airflow between the entry differential force chamber and the second differential force chamber. The flexible membrane may also operate as a third check valve to regulate airflow between the first differential force chamber and the second differential force chamber.

In another aspect, a relief valve is provided to selectively sealingly separate the first differential chamber and a venting port. The relief valve selectively connects the first differential chamber and the venting port in order to deflate the cuff before removal of the respiratory device. The relief valve includes an umbrella-type valve positioned over a channel extending between first differential chamber and the venting port.

In yet another aspect, the valve includes a first valve housing portion defining the entry port and a second valve housing portion defining the first exit port, the second exit port, and the venting port. The flexible membrane may be clamped between the first valve housing portion and the second valve housing portion.

In another aspect, the first valve housing portion defines a projection and the flexible membrane defines a first opening, and the projection includes a first annular web pretensioning the flexible membrane towards the first exit port and surrounding the first opening in the flexible membrane. Thus, the entry differential force chamber is selectively connected to the first differential force chamber via the first opening in the flexible membrane. The first valve housing portion also defines a second annular web having a larger diameter than the first annular web, and the second annular web pretensions the flexible membrane towards the first exit port. Additionally, the second valve housing portion defines a third annular web having a diameter larger than that of the first annular web and smaller than that of the second annular web. The third annular web pretensions the flexible membrane towards the entry port. Furthermore, the flexible membrane defines a second opening positioned radially outwardly from the second annular web such that the entry differential force chamber is selectively connected to the second differential force chamber via the second opening in the flexible membrane.

In yet another aspect, the pressurized air reservoir includes a reservoir housing and pre-formed rubber bellows positioned within the reservoir housing. The reservoir housing and the second valve housing portion may define a single, unitary component.

DETAILED DESCRIPTION OF THE DRAWINGS AND THE PRESENTLY PREFERRED EMBODIMENTS

Figure 1:
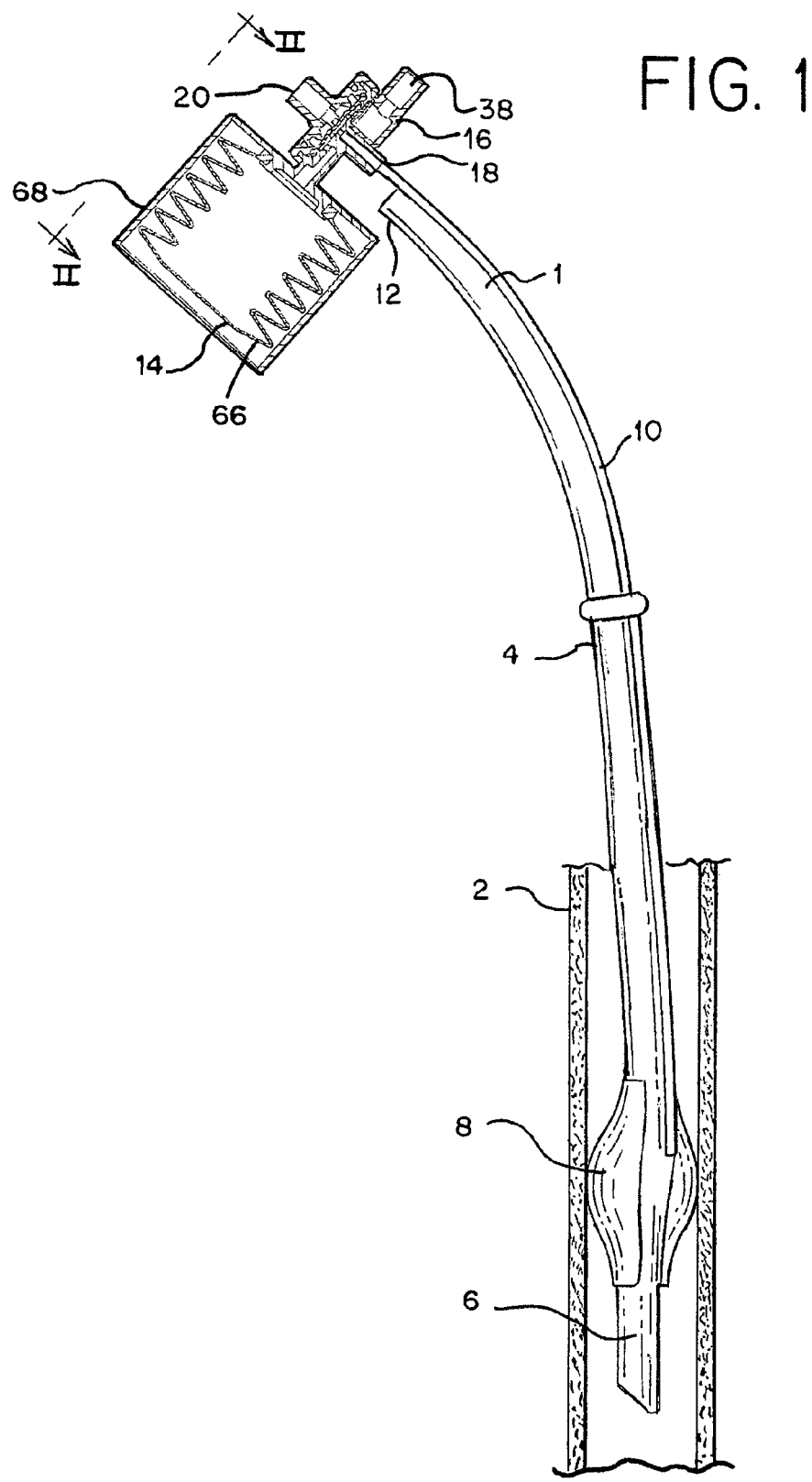
FIG. 1 is a partial-section, schematic view of an embodiment.
Figure 2:
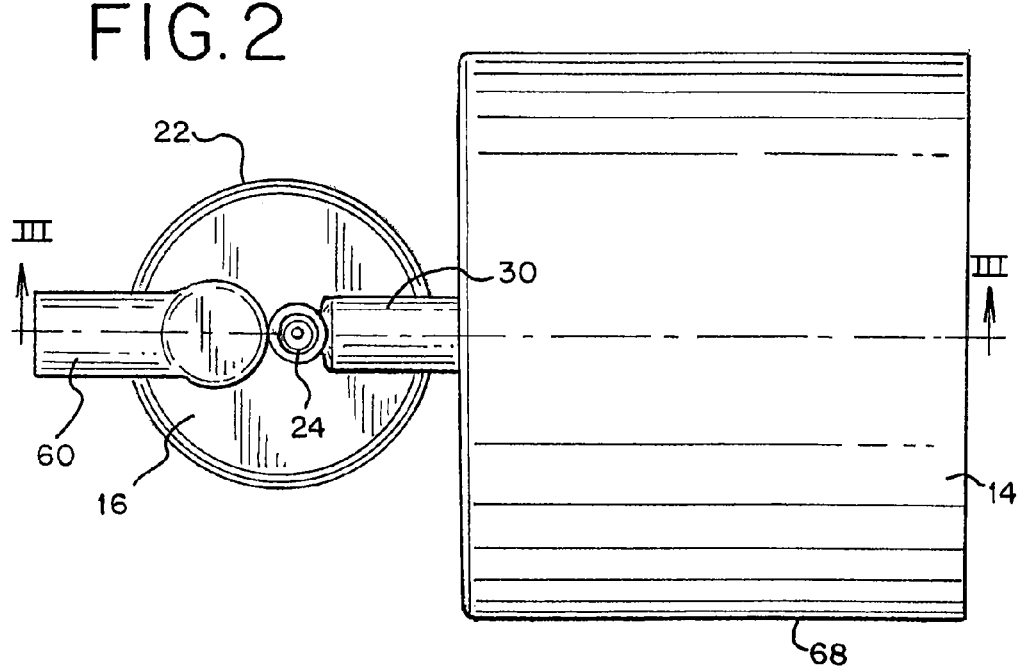
FIG. 2 an exterior view of the apparatus shown in FIG. 1 in the direction of the arrow generally indicated by II.

Referring now to preferred embodiments, FIG. 1 shows one embodiment, generally designated by 1, for connecting a respiratory device (not shown) with a patient's trachea 2. The apparatus 1 includes a flexible breathing tube 4 insertable into the patient's trachea 2 and connectable with a source of breathing gas, such as air or oxygen. Specifically, the proximal end 12 of the breathing tube 4 is connected to a respiratory device. The breathing tube 4 supplies breathing gas to the patient's lungs in regular intervals. The breathing tube 4 is preferably an endotracheal tube or a tracheostomy tube.

An inflatable cuff 8 surrounds a portion of the breathing tube 4 adjacent to the distal end 6 of the breathing tube 4. The cuff 8 includes an air chamber surrounding the breathing tube 4. In its collapsed state, the cuff 8 is collapsed against breathing tube 4 such that the cuff and the breathing tube 4 are able to be inserted into the trachea. To this end, the surgeon selects a diameter of the breathing tube 4 based on the diameter of the trachea. In order to inflate the cuff 8 for forming a seal with the wall of the trachea 2, the distal end of a relatively small connection line 10 is connected with the inside of the cuff 8. Additionally, the proximal end 18 of the connection line 10 is connected to an elastic pressurized air reservoir 14 via a valve 16, as will be discussed further below.

The valve 16 is preferably at least a three-way-valve and it is positioned between the proximal end 18 of the connection line 10 and the pressurized air reservoir 14. The valve 16 includes an entry port 20, a first exit 24, and a second exit 26. Pressurized air can be introduced to the cuff 8 via the entry port 20. For example, a suitable device, such as a syringe, may be inserted into a connector 64 to deliver air to the cuff 8 via an entry port 20 of the valve. The first exit 24 is connected to the connection line 10 and the second exit 26 is connected to the pressurized air reservoir 14.

According to one embodiment of the invention, the valve 16 operates as a three-way check valve and as a differential pressure valve 16, as will be discussed in more detail below. At the entry port 20, the valve 16 operates as a first check valve that closes automatically when the syringe is removed to prevent air from exiting the cuff 8.

As will also be discussed further below, the valve 16 is able to selectively connect the cuff 8 and the pressurized air reservoir 14 to maintain a generally constant pressure within the cuff 8.

Figure 4:
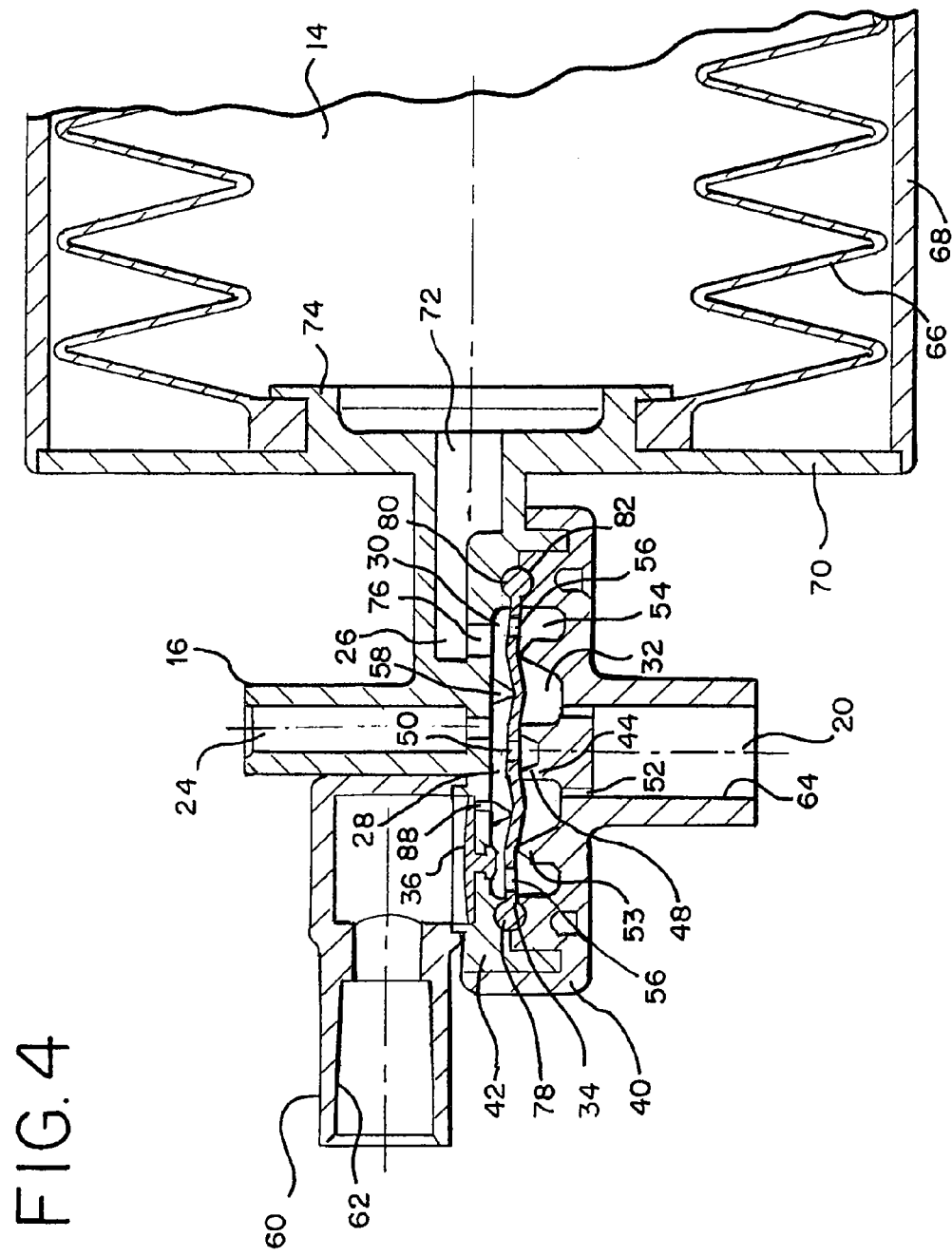
FIG. 4 an enlarged view of a portion of the valve shown FIG. 3.

As best shown in FIG. 4, the valve 16 includes the first exit 24 associated with a first differential force chamber 28; a second exit 26 associated with a second force chamber 30; and an entry port 20 associated with a third differential force chamber 32. The differential force chambers 28, 30 and 32 are selectively sealingly separated from each other by a membrane disk 6.

Additionally, the first differential force chamber 28 of the first exit 24 are connected with a relief valve 36 having an exit 38 by the means of which the relief valve 36 for the decompression of the cuff 8 can be activated by means of vacuum which is more fully described further below.

The housing of the differential pressure valve 16 includes two valve housing halves 40 and 42 sealingly connected with each other. The first valve housing half 40 defines the entry port 20 and the second housing half 42 defines two exits 24 and 26 as well as the relief valve 36. The membrane disk 34 is clamped between the first and the second valve housing half 40 and 42. Each of the housing halves is preferably a single, unitary component produced by injection molding of a plastic material.

A pin-like projection 44 is defined by the first valve housing half 40 and is positioned within the first differential force chamber 28. A first annular web 48 is formed on the top end of the projection 44. The projection 44 and the annular web 48 pretension the membrane disk 34 in the direction of the first exit 24, and the annular web 48 surrounds an opening 50 provided in the membrane disk 34.

Connection channels 52 are provided in the first valve housing half 40, radially exterior of the projection 44. The connection channels 52 connect the entry port 20 and the entry differential force chamber 32. The entry differential force chamber 32 further is limited at the circumference thereof by a second annular web 53 which is preferably unitarily formed with the first housing half 40 and which has a larger diameter than the first annular web 48. The second annular web 53 also pretensions the membrane disk 34 in the direction of the first exit.

The entry differential force chamber 32 therefore is defined by the annular space between the first annular web 48 and the second annular web 53 and by the parts of the membrane disk 34 contacting the webs 48, 53. The entry differential force chamber 32 defines the entry chamber for air when filling the cuff 8 and the pressurized air reservoir 14, and the membrane disk 34 operates as: a first check valve between the entry differential force chamber 32 and the first differential force chamber 28; a second check valve between the entry differential force chamber 32 and the second differential force chamber 30; and a third check valve between the first differential force chamber 28 and the second differential force chamber 30.

Figure 3:
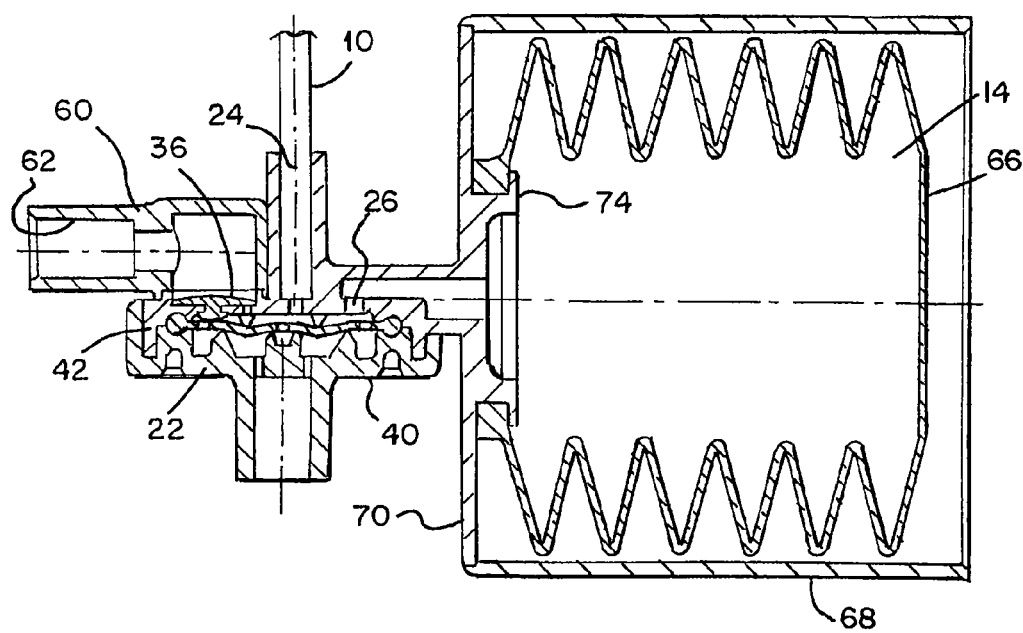
FIG. 3 a cross-sectional view of the valve taken along the line III-III in FIG. 2.

As best shown in FIGS. 3 and 4, the first exit 24 is positioned parallel and generally coaxial to the entry port 20 when the two valve housing halves 40 and 42 are connected with each other.

In the first housing half 40, an annular space 54 is formed radially exterior of the second annular web 53. The annular space is connected to the second differential force chamber 30 by openings 56 in the membrane disk 34.

In the second valve housing half 42, the first exit 24 is associated with the first differential force chamber 28. Also, a third annular web 58 is provided which surrounds the first exit 24. The third annular web 58 pretensions the membrane disk 34 in the direction of the entry port 20 (against the pretension created by the annular webs 48 and 53). The diameter of the third annular web 58 is larger than the diameter of the first annular web 48 and smaller than the diameter of the second annular web 53. Therefore, the first differential force chamber 28 is defined by the space delimited by the third annular web 58 and the corresponding parts of the membrane disk as well as by the space within the first annular web 48 connected by the openings 50.

As best shown in FIG. 4, the relief valve 36 can be opened to the ambient air, thereby connecting the first differential force chamber 28 to the ambient air. A connector 62 is connected with the second housing half 42 and a syringe can be inserted into the connector 62 for drawing air out of the first differential force chamber 28. Specifically, the relief valve 36 is positioned in the housing 60 and is preferably an umbrella-type valve 84 for facilitating deflation of the cuff 8 and the rubber bellows 66. The elastic membrane 86 forming the umbrella head covers one or more connecting channels 88 between the interior of the housing 60 and the first differential force chamber 28. When a syringe is inserted into the connector 62 of the housing 60 in an air-tight manner and the plunger is drawn back, then the vacuum created in the interior of the housing 60 lifts the elastic membrane 86 such that the connecting channels 88 are opened and that the vacuum created thereby in the first differential force chamber 28 and the second differential force chamber 30 lifts the membrane disk 34 from the annular web 58 such as to remove the air contained in the cuff 8 and the air contained in the rubber bellows 66. The relief valve 36 also serves as a safety valve for preventing or minimizing overpressurization of the cuff 8. Specifically, the relief valve 36 may be configured to permit the release of air if the pressure within the cuff 8 reaches a certain level.

As further shown in the drawings, the pressurized air reservoir 14 may be formed as a rubber bellows 66 connected with the second exit 26 which is positioned in a housing 68. As best shown in FIG. 4, the bottom 70 of the housing 68 and the second housing half 42 define a single, unitary component. A connecting channel 72 leading to the second exit 26 is provided with a suitable coupling member 74 in the bottom 70 of the housing which is surrounding the second exit 26 and which in a form-fit manner is connected with the rubber bellows. To achieve a compact construction, the exit opening 76 of the second differential force chamber 30 extends in an angle with respect to the connection channel 72.

In the exemplary embodiment, the membrane disk 34 at a circumference thereof is formed with a unitary annular protrusion 78 which is received in oppositely positioned annular recesses 80 and 82 in the valve housing halves 40 and 42 when the valve housing halves 40 and 42 are connected with each other.

During operation of the apparatus, the breathing tube 4 is inserted into the trachea 2 of the patient. Once the cuff 8 is positioned within the trachea 2 as desired, the cuff 8 and the pressurized air reservoir 14 are inflated as desired. Specifically, a syringe or other appropriate device is connected to the entry port 20 and an inflating gas such as air or oxygen is delivered to the entry differential force chamber 32 via the connection channels 52. For example, approximately 40 to 50 milliliters of air is introduced to the entry port 20 such that the membrane disk 34 is lifted upward from the first annular web 48, which allows air to flow through the opening 50, into the first differential force chamber 28, and into the cuff 8. Simultaneously, the membrane disk 34 also lifts upward from the second annular web 53, which allows air to flow through the openings 56, into the second differential force chamber 30, and into the pressurized air reservoir 14.

After the injection of airflow from the syringe, the membrane disk 34 reengages the first and second annular webs 48, 53, thereby operating as the first and second check valve, respectively. Specifically, the air in the cuff 8 and the pressurized air reservoir 14 is prevented from exiting the entry port 20 due to respective seals between the membrane disk 34 and the first and second annular webs 48, 53.

In this state, the cuff 8 maintains a generally constant pressure, such that the respective components 8, 66 have the same air pressure. For example, if the air pressure in the cuff 8 changes, such as if the patient moves applies pressure to the cuff 8 or if excess respiration air acts on the outer surface of the cuff 8, air is able to flow from the cuff 8 to the rubber bellows 66. The membrane disk 34 and the third annular web 58 cooperate to define the third check valve and a differential pressure valve. Specifically, an unbalanced air pressure between the cuff 8 and the rubber bellows 66 causes the membrane disk 34 to deflect downward off of the third annular web 58, thereby temporarily connecting the first and second differential force chambers 28, 30. The rubber bellows 66 in this design serves as a pressurized air reservoir 14.

Conversely, when the pressure in the cuff 8 decreases, such as due to respiration or movement of the patient, the pressure in the first exit 24 is smaller than the pressure in the second exit 26 such that this pressure acting in the second differential force chamber again can lift the membrane disk 34 from the third annular web 58 and the air can flow back into the cuff 8 through the exit 24 and the connecting line 10, wherein in this direction the flow is meeting a substantially smaller resistance compared with a flow from the cuff 8 since the available area of the membrane disk 24 in the second differential force chamber is substantially larger.

In the above-described embodiment, the cuff 8 is able to maintain a generally constant seal with the trachea, despite varying factors such as movement of the patient or changes in pressure in the patient's trachea.

It is therefore intended that the foregoing detailed description be regarded as illustrative rather than limiting, and that it be understood that it is the following claims, including all equivalents, are intended to define the spirit and scope of this invention. More particularly, the apparatus and assembly described are merely an exemplary apparatus and assembly, and they are not intended to be limiting. Many of the steps and devices for performing the steps described above may be eliminated or replaced by alternative steps and devices.

What is claimed is:

1. An apparatus for connecting a respiratory device with a patient, the apparatus comprising:
   a breathing tube having a proximal end and a distal end configured to be inserted into a trachea of the patient;
   an inflatable cuff positioned around a portion of the breathing tube;
   a connection line having a proximal end and a distal end connected to the cuff;
   a pressurized air reservoir located adjacent to the proximal end of the connection line, the pressurized air reservoir having an adjustable volume; and
   a valve connected to the pressurized air reservoir and to the proximal end of the connection line, the valve including:
      a first valve housing portion defining a projection and an entry port associated with an entry differential force chamber and configured to be coupled with a syringe;
      a second valve housing portion defining a first exit port associated with a first differential force chamber and configured to be coupled with the proximal end of the connection line;
      a second exit port associated with a second differential force chamber and configured to be coupled with the pressurized air reservoir; and
      a flexible membrane selectively sealingly separating the first differential force chamber, the second differential force chamber, and the entry differential force chamber from each other, wherein the flexible membrane is configured to selectively connect the first differential force chamber and the second differential force chamber so as to maintain a substantially constant air pressure in the cuff,
   wherein the flexible membrane defines a first opening and the projection includes a first annular web configured to pretension the flexible membrane towards the first exit port and configured to surround the first opening in the flexible membrane.

2. An apparatus as in claim 1, wherein the flexible membrane is a three-way check valve.

3. An apparatus as in claim 2, wherein the flexible membrane is configured to operate as a first check valve to regulate airflow between the entry differential force chamber and the first differential force chamber.

4. An apparatus as in claim 3, wherein the flexible membrane is configured to operate as a second check valve to regulate airflow between the entry differential force chamber and the second differential force chamber.

5. An apparatus as in claim 4, wherein the flexible membrane is configured to operate as a third check valve to regulate airflow between the first differential force chamber and the second differential force chamber.

6. An apparatus as in claim 1, further comprising a relief valve selectively sealingly separating the first differential chamber and a venting port.

7. An apparatus as in claim 6, wherein the relief valve is configured to selectively connect the first differential chamber and the venting port to deflate the cuff.

8. An apparatus as in claim 7, wherein the relief valve includes an umbrella-type valve positioned over a channel extending between first differential chamber and the venting port.

9. An apparatus as in claim 6, wherein the relief valve is configured to permit the release of air from the cuff when an air pressure within the cuff exceeds a desired level.

10. An apparatus as in claim 1, wherein the second valve housing portion defines the second exit port.

11. An apparatus as in claim 10, wherein the flexible membrane is clamped between the first valve housing portion and the second valve housing portion.

12. An apparatus as in claim 10, the first annular web configured to pretension the flexible membrane towards the first exit port and configured to surround the first opening in the flexible membrane, such that the entry differential force chamber is selectively connected to the first differential force chamber via the first opening in the flexible membrane.

13. An apparatus as in claim 12, wherein the first valve housing portion defines a second annular web having a larger diameter than the first annular web, the second annular web configured to pretension the flexible membrane towards the first exit port; and
   wherein the second valve housing portion defines a third annular web having a diameter larger than that of the first annular web and smaller than that of the second annular web, the third annular web configured to pretension the flexible membrane towards the entry port.

14. An apparatus as in claim 13, wherein the flexible membrane defines a second opening positioned radially outwardly from the second annular web such that the entry differential force chamber is selectively connected to the second differential force chamber via the second opening in the flexible membrane.

15. An apparatus as in claim 14, wherein the first valve housing portion defines an annular space positioned radially outwardly from the second annular web such that the entry differential force chamber is selectively connected to the second differential force chamber via the annular space and the second opening in the flexible membrane.

16. An apparatus as in claim 10, wherein the pressurized air reservoir includes a reservoir housing and pre-formed rubber bellows positioned within the reservoir housing.

17. An apparatus as in claim 16, wherein the reservoir housing and the second valve housing portion define a single, unitary component.

18. An apparatus as in claim 10, wherein the flexible membrane includes an annular protrusion at the circumference thereof, wherein the first valve housing portion and the second valve housing portion cooperate to define an annular recess, and wherein the annular protrusion of the flexible membrane is received within the annular recess.

19. An apparatus for connecting a respiratory device with a patient, the apparatus comprising:
   a breathing tube having a proximal end and a distal end configured to be inserted into a trachea of the patient;
   an inflatable cuff positioned around a portion of the breathing tube;
   a connection line having a proximal end and a distal end connected to the cuff;
   a pressurized air reservoir located adjacent to the proximal end of the connection line, the pressurized air reservoir having an adjustable volume; and
   a valve connected to the pressurized air reservoir and to the proximal end of the connection line, the valve including:
      a first valve housing portion defining a projection and an entry port associated with an entry differential force chamber and configured to be coupled with a syringe;
      a second valve housing portion defining a first exit port associated with a first differential force chamber and configured to be coupled with the proximal end of the connection line;

a second exit port associated with a second differential force chamber and configured to be coupled with the pressurized air reservoir; and a flexible membrane selectively sealingly separating the first differential force chamber, the second differential force chamber, and the entry differential force chamber from each other, the flexible membrane configured to operate as a three-way check valve.

wherein the flexible membrane defines a first opening and the projection includes a first annular web configured to pretension the flexible membrane towards the first exit port and configured to surround the first opening in the flexible membrane.

20. An apparatus as in claim 19, wherein the flexible membrane is configured to operate as a first check valve to regulate airflow between the entry differential force chamber and the first differential force chamber, wherein the flexible membrane is configured to operate as a second check valve to regulate airflow between the entry differential force chamber and the second differential force chamber, and wherein the flexible membrane is configured to operate as a third check valve to regulate airflow between the first differential force chamber and the second differential force chamber.

* * * * *

UNITED STATES PATENT AND TRADEMARK OFFICE
CERTIFICATE OF CORRECTION

| | | |
|---|---|---|
| PATENT NO. | : 7,717,116 B2 | Page 1 of 1 |
| APPLICATION NO. | : 11/633271 | |
| DATED | : May 18, 2010 | |
| INVENTOR(S) | : Jan W. Mijers | |

It is certified that error appears in the above-identified patent and that said Letters Patent is hereby corrected as shown below:

In column 7, claim 1, line 32, after "cuff" replace the "," with a --;--

In column 9, claim 19, line 8, after "valve" replace the "." with a --;--

Signed and Sealed this

Seventeenth Day of August, 2010

David J. Kappos
*Director of the United States Patent and Trademark Office*